United States Patent
Kinoshita et al.

(10) Patent No.: US 6,280,434 B1
(45) Date of Patent: *Aug. 28, 2001

(54) ANGIOGRAPHIC CATHETER

(75) Inventors: Yasushi Kinoshita, Fujinomiya; Makoto Takamiya, Toyonaka, both of (JP)

(73) Assignee: Terumo Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/015,953

(22) Filed: Jan. 30, 1998

(30) Foreign Application Priority Data

Jan. 31, 1997 (JP) .................................. 9-032940

(51) Int. Cl.[7] .................................. A61M 25/00
(52) U.S. Cl. ...................... 604/530; 604/264; 600/435
(58) Field of Search ...................... 604/264, 280, 604/281, 282, 523, 530, 534, 532, 528; 600/433–435

(56) References Cited

U.S. PATENT DOCUMENTS

| | | | |
|---|---|---|---|
| 4,547,193 | * 10/1985 | Rydell | 604/282 |
| 4,619,247 | 10/1986 | Inoue et al. . | |
| 4,694,838 | 9/1987 | Wijayarthna et al. . | |
| 4,717,387 | 1/1988 | Inoue et al. . | |
| 4,735,620 | * 4/1988 | Ruiz | 604/281 |
| 4,747,840 | * 5/1988 | Ladika et al. | 604/281 |
| 4,874,360 | * 10/1989 | Goldberg et al. | 604/8 |
| 4,898,591 | * 2/1990 | Jang et al. | 604/282 |
| 4,913,683 | * 4/1990 | Gregory | 604/8 |
| 4,950,228 | * 8/1990 | Knapp, Jr. et al. | 604/8 |
| 4,957,479 | * 9/1990 | Roemer | 604/8 |
| 4,961,731 | * 10/1990 | Bodicky et al. | 604/264 |
| 5,037,403 | * 8/1991 | Garcia | 604/280 |
| 5,061,257 | * 10/1991 | Martinez et al. | 604/282 |
| 5,163,431 | * 11/1992 | Griep | 604/282 |
| 5,201,723 | * 4/1993 | Quinn | 604/264 |
| 5,630,823 | * 5/1997 | Schmtz-Rode et al. | 606/128 |

FOREIGN PATENT DOCUMENTS

| | | |
|---|---|---|
| 0 346 012 | 12/1989 | (EP) . |
| 0 411 605 | 2/1991 | (EP) . |
| 0 609 950 | 8/1994 | (EP) . |
| 6-114113 | 4/1994 | (JP) . |
| 6-38857 | 5/1994 | (JP) . |
| 8-98890 | 4/1996 | (JP) . |
| 0609950 | * 10/1994 | (NL) . |

* cited by examiner

Primary Examiner—Richard K. Seidel
Assistant Examiner—Loan H. Thanh
(74) Attorney, Agent, or Firm—Burns, Doane, Swecker & Mathis, LLP

(57) ABSTRACT

An angiographic catheter has exhibits elasticity as a whole and has at a distal end portion thereof a deformed portion that is curved into a desired shape when no external force is applied thereto. The deformed portion has at a distal end thereof a distal end opening. A plurality of minute side apertures are formed in a portion that is located toward a proximal end of the catheter from the deformed portion. These side apertures are arranged such that a reaction force generated by injection of a contrast medium (liquid) fed through a lumen of the catheter from the distal end opening is counterbalanced to the greatest possible extent by the contrast medium (liquid) injected from the respective side apertures.

30 Claims, 9 Drawing Sheets

ANGIOGRAPHIC CATHETER

This application claims priority under 35 U.S.C. §§ 119 and/or 365 to Japanese Patent Application No. 032,940 filed in Japan on Jan. 31, 1997, the entire content of which is hereby incorporated by reference.

BACKGROUND OF THE INVENTION

1. Field of the Invention

The present invention relates to an angiographic catheter for use in radiography of a lumina of a human such as a heart, a blood vessel of surrounding the heart, a liver, a pancreas, a bile duct and the like.

2. Description of the Related Art

In general, a Judkins type catheter or an Anplatz type catheter has been employed to form an image of a coronary artery, whereas a pigtail type catheter has been employed to form a X-ray image of a left ventricle.

For example, the pigtail type catheter is introduced into a blood vessel near the left ventricle from a femoral artery using a Seldinger method or a sheath method. A guide wire is inserted into the catheter so that the catheter is able to proceed, retreat, rotate or perform other motions. The catheter thereby selects a desired path from a plurality of branching blood vessels and reaches an ascending artery. Thereafter, a distal end portion of the catheter that is curved like a loop is inserted into the left ventricle. In this state, a contrast medium is fed from a proximal end portion of the catheter and injected into the left ventricle in order to form an image thereof.

FIG. 4 is a perspective view illustrating the construction of the generally employed pigtail type catheter, and FIG. 5 is a perspective view illustrating a state where the contrast medium is injected from the catheter as illustrated in FIG. 4.

As illustrated in these figures, the generally employed pigtail type catheter 11 has a distal end opening 13 and a plurality of side apertures 14. The side apertures 14 are located toward the proximal end portion of the catheter 11 from a loop-like deformed portion 12. Hence, a contrast medium 8 is injected from the distal end opening 13 and the respective side apertures 14.

In this case, the respective side apertures 14 are formed perpendicularly to an outer peripheral wall of the catheter 11. However, the contrast medium 8, which is fed under a high pressure, is not injected perpendicularly to the outer peripheral wall of the catheter 11 but obliquely toward the distal end of the catheter 11 (See arrows as illustrated in FIG. 5). This is because the side apertures 14 have a relatively large diameter (0.9 mm).

Hence, a reaction force generated by injection of the contrast medium 8 moves (or displaces) the distal end portion of the catheter 11 toward the proximal end portion of the catheter 11, that is, toward a sinus of Valsalva. Also, the reaction force generated by injection of the contrast medium 8 from the distal end opening 13 of the catheter 11 moves the distal end portion of the catheter 11 laterally, that is, in a direction in which the loop-like deformed portion 12 extends. Consequently, the catheter 11 moves diagonally upward from a location indicated by a dashed line of FIG. 5 (to a location indicated by a solid line).

In the case where injection of the X-ray contrast medium causes such a movement of the catheter, the distal end portion of the catheter tends to be detached from a desired part (left ventricle), and it is impossible to feed the contrast medium into the desired part appropriately and uniformly. As a result, the function of X-ray image formation becomes insufficient.

Although some of the generally employed angiographic catheters are provided with a plurality of side apertures, the number of the side apertures formed in an arbitrary portion of the catheter with an axial length of 10 mm is at most 6. Because the side apertures are arranged at long intervals, the contrast medium injected from the respective side apertures cannot flow into a space corresponding to the desired part uniformly. In order to enhance the function of image formation sufficiently, it is inevitable to increase a flow rate of the contrast medium. In this case, the contrast medium flowing out of the respective side apertures intensely stimulates the lumina of a human.

SUMMARY OF THE INVENTION

It is a first object of the present invention to provide an angiographic catheter which is able to perform the operation of image formation appropriately by inhibiting the catheter from being moved or displaced by injection of a contrast medium.

In order to achieve the first object, there is provided an angiographic catheter exhibiting elasticity and having at a distal end portion thereof a deformed portion that is curved into a desired shape when no external force is applied thereto, the deformed portion having at a distal end thereof a distal end opening, wherein a plurality of minute side apertures are formed in a portion that is located toward a proximal end of the catheter from the deformed portion, and wherein the side apertures are arranged such that a reaction force generated by injection of a liquid fed through a lumen of the catheter from the distal end opening is counterbalanced to the greatest possible extent by the liquid injected from the respective side apertures.

It is a second object of the present invention to provide an angiographic catheter which is able to feed the contrast medium uniformly into a space corresponding to a desired part of a lumina of a human reduce the amount of the contrast medium required to perform the operation of image formation sufficiently, weaken the impetus of the contrast medium flowing out of the respective side apertures and alleviate a stimulus imparted to the lumina of a human.

In order to achieve the second object, there is provided an angiographic catheter including a catheter tube having a lumen, a distal end opening that communicates with the lumen, and side apertures that communicate with the lumen, wherein the side apertures are provided to a predetermined section of a flank of a distal end portion of the catheter tube, and wherein the number of the side apertures formed in an arbitrary section of the predetermined section with an axial length of 10 mm is greater than 9, each of the side apertures covering an area smaller than 0.3 mm$^2$.

BRIEF DESCRIPTION OF THE DRAWINGS

Further objects, features and advantages of the present invention will become apparent from the following description of the preferred embodiments with reference to the accompanying drawings, wherein.

DESCRIPTION OF PREFERRED EMBODIMENTS

Figure 1:
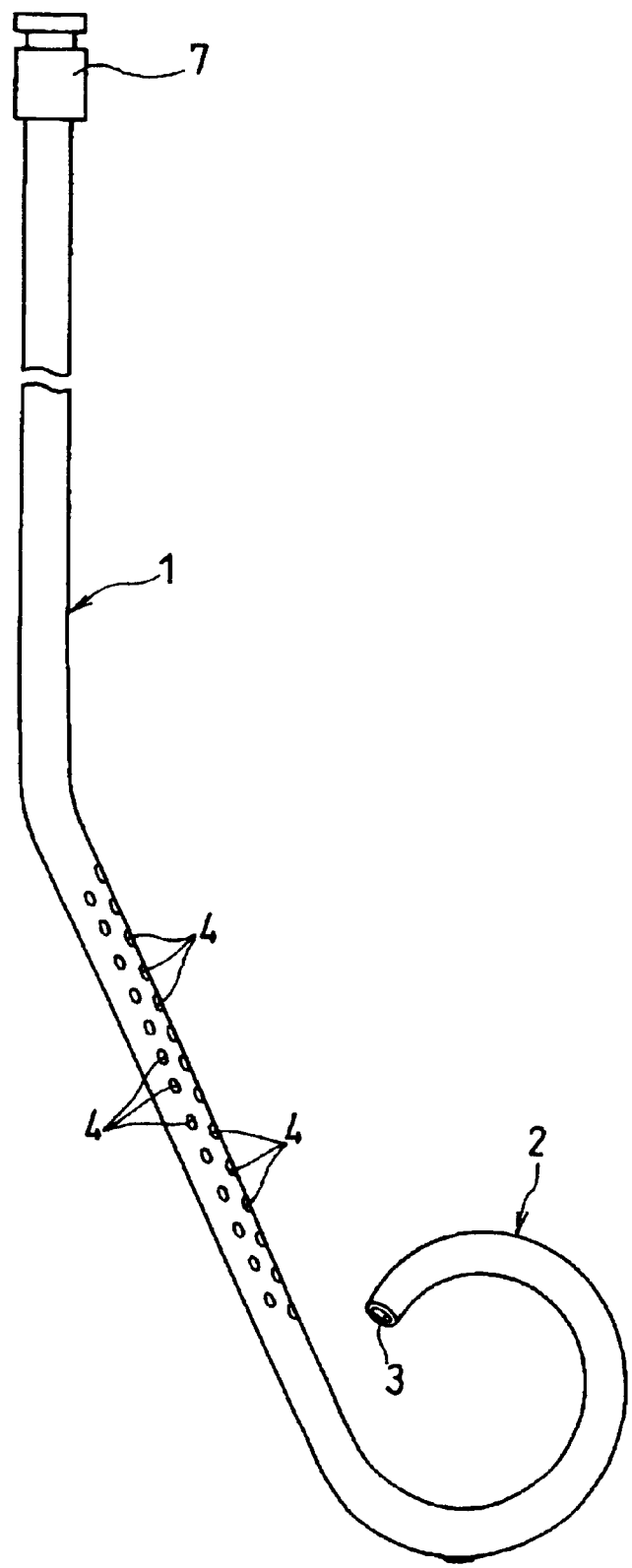
FIG. 1 is a partially omitted perspective view illustrating an angiographic catheter according to the present invention.

Preferred embodiments of an angiographic catheter according to the present invention will be described hereinafter with reference to the accompanying drawings.

It is apparent from these drawings that an angiographic catheter 1 (hereinafter referred to simply as "catheter") according to the present invention is a pigtail type catheter. In other words, the catheter 1 exhibits elasticity as a whole and has a distal end portion thereof a deformed portion 2. The deformed portion 2 is curved like a loop when no external force is applied thereto.

The catheter 1 may be made of a polyolefin such as polyethylene, polypropylene and a copolymer of ethylene and vinyl acetate, a polyolefin elastomer thereof, a polyamide resin (such as nylon 11, nylon 12 and nylon 6), a polyester polyamide resin (such as Grilax, a product of DIC Corp.), a polyeter polyamide resin (such as Pebax, a product of Atochem Corp.), polyurethane, ABS resin, a fluorine resin (such as PFA, PTFE and ETFE) or a soft fluorine resin, polyimide, a shape-memory resin, or various synthetic resins such as a polymer blend or a polymer alloy including the aforementioned materials (such as a polymer alloy of polyamide elastomer and polyurethane). The catheter 1 is inserted into a lumina of a human, at which X rays are beamed to identify a location thereof. Therefore, the catheter 1 may include a X-ray opaque substance such as barium sulfate, bismuth oxide and tungsten.

Formed inside the catheter 1 is a lumen through which a liquid such as a contrast medium flows. The lumen opens at a distal end of the catheter 1, thus constituting a distal end opening 3. A guide wire (not shown) is inserted into the lumen, for example, when the catheter 1 is inserted into the lumina of a human of any other conduit including a heart, arteries, veins, vessels and a biliary tree.

Although not limited to any specific value, the catheter 1 has an outer diameter ranging preferably from 0.8 mm to 3.0 mm, more preferably, from 1.0 mm to 2.5 mm. The loop-like deformed portion 2 has a radius ranging preferably from 3.0 mm to 15.0 mm, more preferably, 3.0 mm to 8.0 mm.

Although not limited to any specific value, the catheter 1 has a thickness (=(outer diameter−inner diameter)/2) ranging preferably from 0.1 mm to 0.7 mm, more preferably, from 0.15 mm to 0.5 mm.

The catheter 1 has a plurality of minute side apertures 4 which are located toward a proximal end portion of the catheter 1 from the deformed portion 2. These side apertures 4 are arranged such that a reaction force generated by injection or extrusion of the contrast medium (liquid) 8 from the distal end opening 3 is counterbalanced to the greatest possible extent by the X-ray contrast medium (liquid) 8 injected or extruded from the respective side apertures 4.

Figure 2:
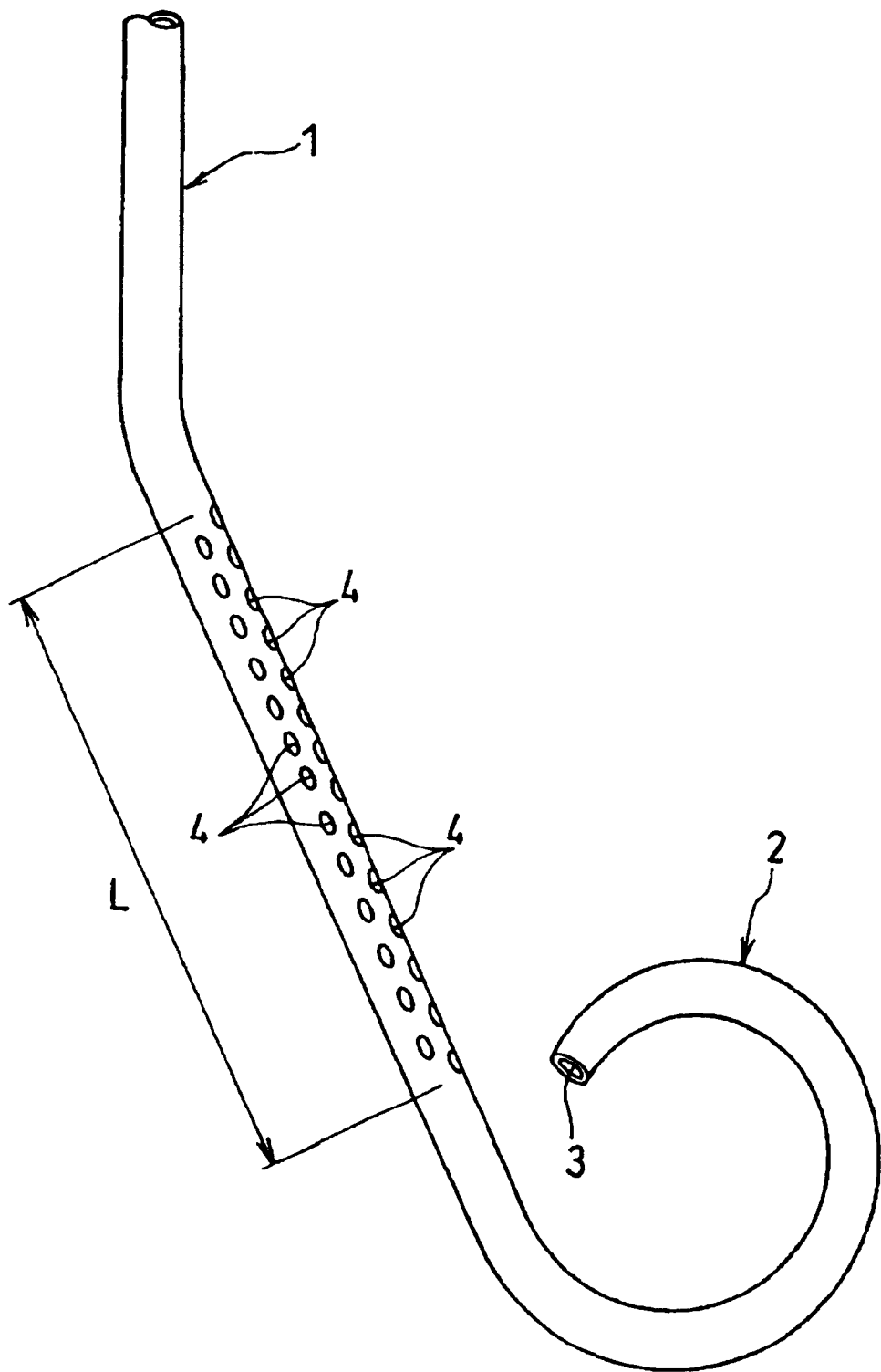
FIG. 2 is a perspective view illustrating an example of construction of a distal end portion of the angiographic catheter according to the present invention.

More specifically, as illustrated in FIGS. 1, 2, the side apertures 4 are arranged densely and formed in a flank(in the side wall) of the catheter 1 at which the deformed portion 2 is directed. Thus, the vectorial sum of a jet force generated by the contrast medium 8 injected from the distal end opening 3 and a jet force generated by the contrast medium 8 injected from the respective side apertures 4 becomes approximate to null. As a result, it is possible to inhibit the catheter 1 from being moved by injection of the contrast medium 8.

In this embodiment, the side apertures 4 are formed in the flank of the catheter 1 at which the deformed portion 2 is directed, preferably over a central angle of 180°. The central angle of the side apertures forming area is preferable up to 180°, more preferably, from 100° to 200°

Although not limited to any specific value, a portion of the catheter where the side apertures 4 are formed has an axial length L ranging preferably from 5 mm to 80 mm, more preferably, from 20 mm to 60 mm.

Although not limited to any specific value, the side apertures 4 have a (mean) diameter ranging preferably from 0.06 mm to 0.7 mm, more preferably, from 0.2 mm to 0.7 mm, even more preferably, from 0.4 mm to 0.6 mm. If the side apertures 4 have too large a diameter, the contrast medium 8 tends to be injected from the side apertures 4 not perpendicularly to an axis of the catheter but obliquely toward the distal end thereof. Hence, the reaction force generated by injection of the contrast medium 8 from the side apertures 4 may move the distal end portion of the catheter 1 toward the proximal end portion thereof. On the contrary, if the side apertures 4 have too small a diameter, there arises a great resistance against injection of the contrast medium 8 from the side apertures 4. Consequently, the aforementioned reaction force may not be counterbalanced sufficiently. The loop-like deformed portion 2 has a radius ranging preferably from 3.0 mm to 15.0 mm, more preferably from 3.0 to 8.0 mm.

The side apertures 4 cover an area ranging preferably from 0.003 $mm^2$ to 0.3 $mm^2$, especially, from 0.008 $mm^2$ to 0.28 $mm^2$ and, more preferably, from 0.03 $mm^2$ to 0.25 $mm^2$.

The side aperture may be an axially elongated ellipse or the oval of the catheter. As the side apertures, the ratio of the length of the major axis to the minor axis length is desirably equal to or more than 1.2 and the minor axis length is desirably equal to or more than 0.06 mm. The ratio of the length of the major axis to the minor axis length is more desirably equal to or more than 1.3 and the minor axis length is desirably equal to or more than 0.2 mm. The oval here is the elliptical one which contains a straight line part.

The side apertures are provided so that the major axis of the side apertures is substantially parallel with the axial direction of the catheter. The major axis of the side apertures may be rather diagonal to the axis of the catheter tube. The strength of the side apertures forming part becomes high compared with the case where side apertures of the true circle with approximately the same area by making side apertures of the ellipse or the oval. The side apertures having a shape of the ellipse or the oval cover an area ranging preferably from 0.03 $mm^2$ to 0.3 $mm^2$.

Although not limited to any specific value, the number of the side apertures 4 to be formed ranges preferably from 25 to 200, more preferably, from 70 to 150. If the number of the side apertures 4 to be formed is too small, the aforementioned reaction force may not be counterbalanced sufficiently. On the contrary, if the number of the side apertures 4 to be formed is too large, especially in the case where the side apertures 4 are arranged densely, the portion of the catheter 1 where these side apertures 4 are formed may be weakened.

The density of the side apertures 4 to be formed may or may not be changed in the axial direction of the catheter 1. For example, in the case where the side apertures 4 are arranged densely in the vicinity of the deformed portion 2, a greater counterforce can be obtained which acts against a jet stream of the contrast medium 8 injected from the distal end opening 3.

In the case where a liquid is fed into the catheter 1 through the lumen thereof, the amount of the liquid injected from the distal end opening 3 is defined as Q1 and the total amount of the liquid injected from the respective side apertures 4 is defined as Q2. In this case, the ratio of Q2/(Q1+Q2) ranges preferably from 0.5(50%) to 0.9(90%), more preferably, from 0.55(55%) to 0.8(80)% and, most preferably, from 0.6(60%) to 0.75(75%). In the case where the ratio of Q2/(Q1+Q2) assumes such values, the reaction force generated by the jet stream of the contrast medium injected is counterbalanced sufficiently. It is thus possible to inhibit the movement of the catheter 1 more effectively.

Figure 3:
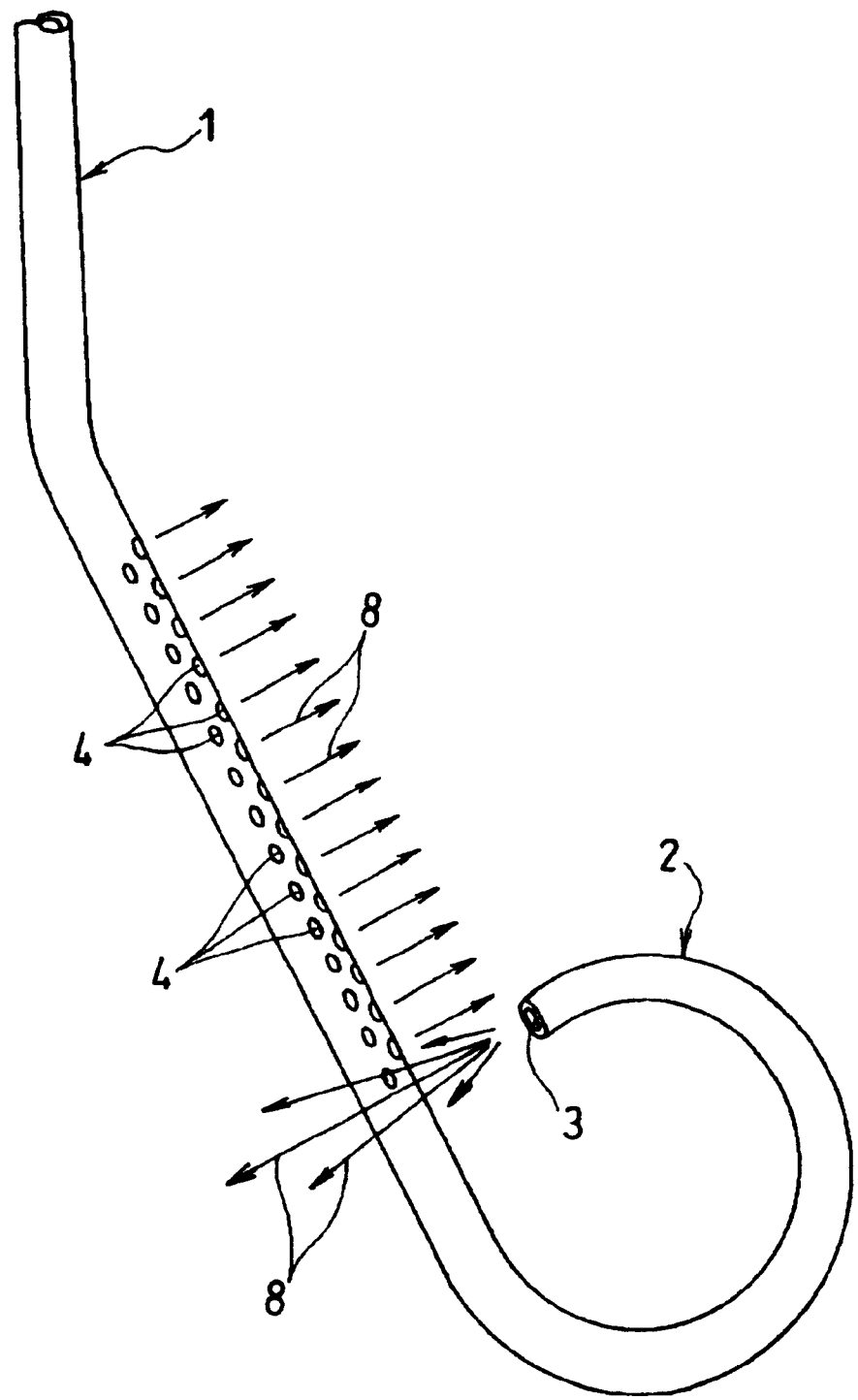
FIG. 3 is a perspective view illustrating a state where a contrast medium is injected from the catheter as illustrated in FIG. 2.
Figure 4:
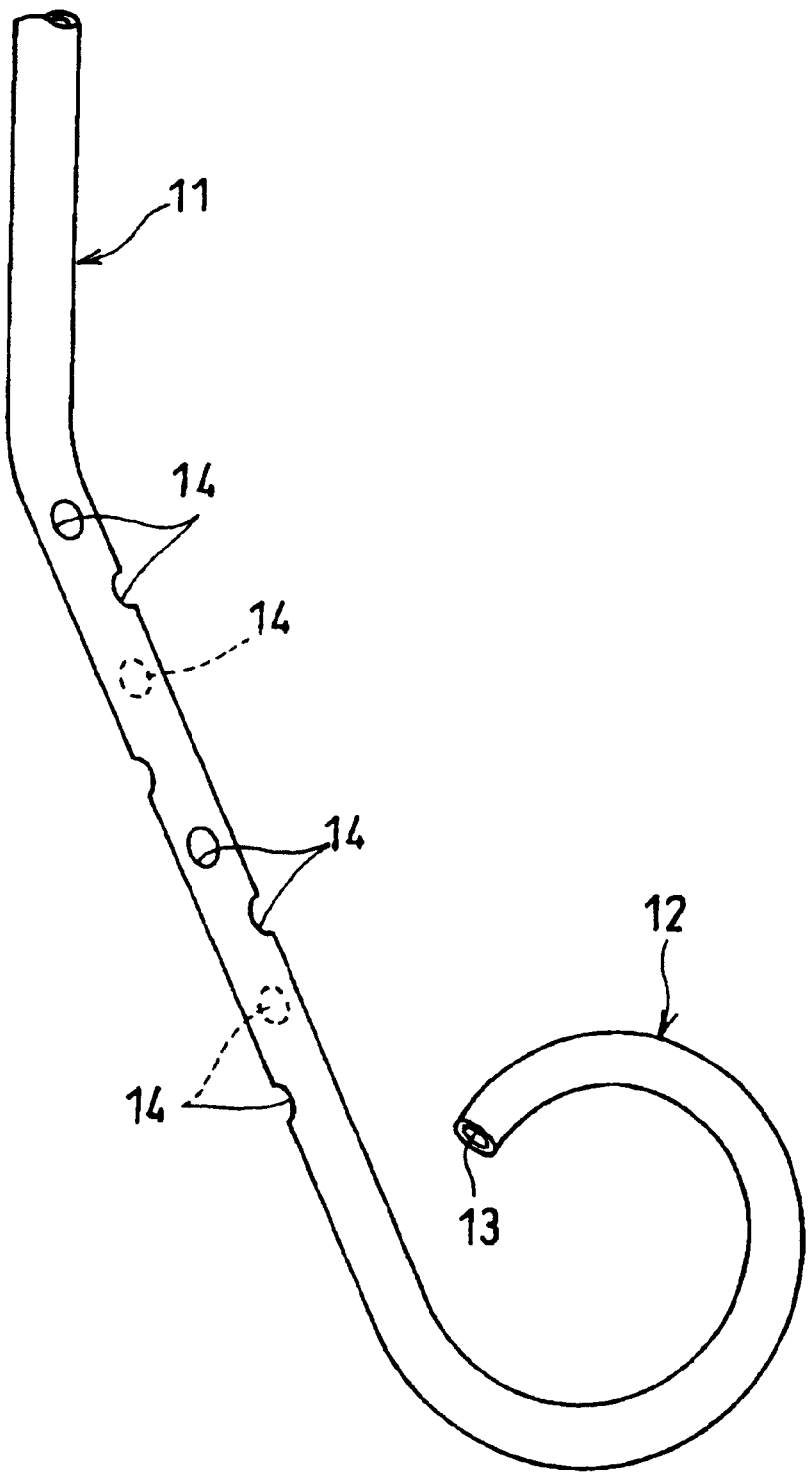
FIG. 4 is a perspective view illustrating a construction of a generally employed pigtail type catheter.
Figure 5:
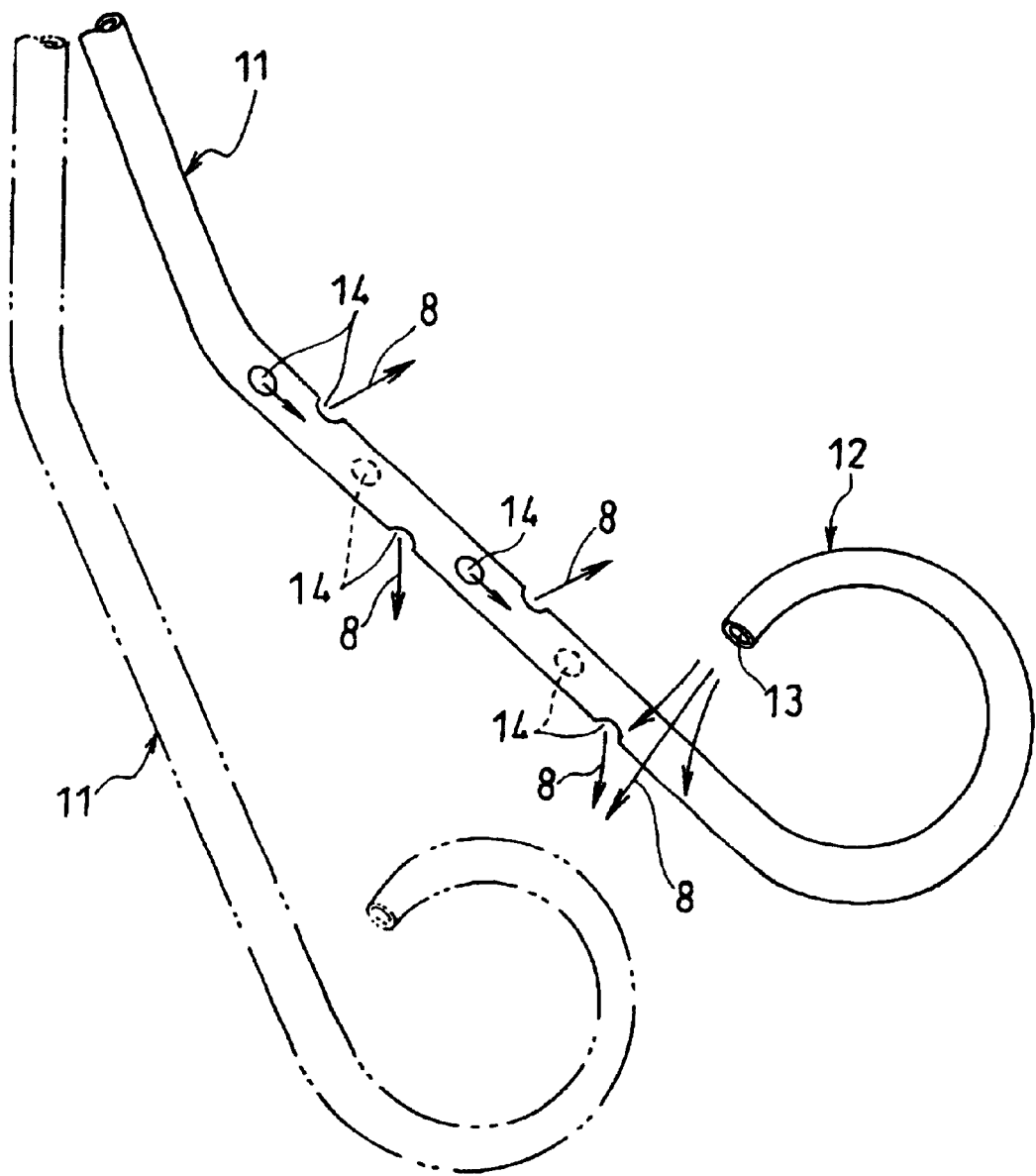
FIG. 5 is a perspective view illustrating a state where a contrast medium is injected from the catheter as illustrated in FIG. 4.

According to the present invention, the catheter 1 is designed such that when the contrast medium 8 is injected from the distal end opening 3, the reaction force generated by the jet stream slightly increases a radius of curvature of the deformed portion 2. Hence, the jet stream of the contrast medium 8 injected from the distal end opening 3 flows substantially perpendicularly to the axis of the portion of the catheter 1 where the side apertures 4 are formed (See FIGS. 2, 3 for comparison).

It is to be noted that according to the present invention, the arrangement of the side apertures 4 is not limited to that as illustrated in the drawings. For example, a small number of side apertures 4 may be formed in a flank portion of the catheter 1 that is opposite to the portion at which the deformed portion 2 is directed.

Although the side apertures 4 can be formed in the catheter 1 by any possible process such as machining, it is especially preferable to utilize laser beam machining. This is because the side apertures 4 can be formed easily and the shape and dimension thereof can be controlled with precision. More preferably, a laser that oscillates at a wavelength within an ultraviolet region, for example, an excimer laser is used.

The excimer laser achieves short pulse oscillation with a high peak power in the ultraviolet region. By combining noble gas (Ar, Kr, Xe, and the like) with halogen (F, Cl, Br, and the like), the excimer laser oscillates, for example, at a wavelength ranging from 193 nm to 351 nm. The excimer laser having such a property allows the side apertures 4 of a small diameter to be formed easily with high processability as well as high precision, without causing process errors such as alteration, meltdown, flash or soot.

Taking into account the materials constituting the catheter 1, the excimer laser that oscillates at a wavelength of less than 248 nm is preferred. More specifically, a KrF excimer laser that oscillates at a wavelength of 248 nm or an ArF excimer laser that oscillates at a wavelength of 193 nm is preferred. Lasers with such a wavelength provide a remarkably high processability.

Needless to say, a solid laser can be employed as a light source, utilizing wavelength conversion technology. The solid laser oscillates at a wavelength within the ultraviolet region.

A hub 7 made of a hard or semi-hard synthetic resin (such as polycarbonate, polypropylene or polyamide) is attached to the proximal end of the catheter 1. A contrast medium injector (such as a syringe) can be attached to a rear end portion of the hub 7.

The examples of the present invention will be described hereinafter more concretely.

EXAMPLE 1

As illustrated in FIG. 2, a pigtail type catheter of Example 1 has been manufactured to form an image of a left ventricle. The respective conditions concerning this catheter are as follows.

The side apertures are formed by laser beam machining using a KrF excimer laser that oscillates at a wavelength of 248 nm (with a power density of 0.5 kW/cm$^2$ on a surface of an object to be processed and with an irradiation time of 2.3 sec for each of the side apertures).

Material constituting the catheter: a polymer alloy of polyamide elastomer and polyurethane mixed with a X-ray opaque substance (barium sulfate)

(Mean) outer diameter of the catheter 1.4 mm (Mean) inner diameter of the catheter: 0.9 mm (Mean) radius of curvature of the loop of the deformed portion: 12 mm Diameter of the distal end opening: 1.0 mm Locations of the side apertures formed: scattered over a portion with a length of 30 mm at which the deformed portion is directed, over a central angle of 180°

The number of the side apertures formed: 95 (5 rows of 19 side apertures)

Diameter of the side apertures: 0.5 mm

EXAMPLE 2

Another catheter of Example 2 has been manufactured, which is similar to that of Example 1 except that the conditions concerning the distal end opening and the side apertures are changed as follows.

Diameter of the distal end opening: 1.0 mm

Locations of the side apertures formed: scattered over a portion with a length of 45 mm at which the deformed portion is directed, over a central angle of 120°

The number of the side apertures formed: 120 (4 rows of 30 side apertures)

Diameter of the side apertures: 0.4 mm

COMPARATIVE EXAMPLE 1

Still another catheter of Comparative example 1 has been manufactured, which is similar to that of Example 1. The conditions concerning the side apertures are changed as follows.

Locations of the side apertures formed: arranged radially (over a central angle of 360°) over a portion with a length of 25 mm The number of the side apertures formed: 10

Diameter of the side apertures: 0.9 mm

EXPERIMENT 1

An experiment has been conducted on each of the aforementioned catheters. This experiment includes the steps of fixing a portion of the catheter 1 which is about 30 cm away from the distal end thereof, feeding a contrast medium (with a viscosity of 10.6 cps) into the catheter from the proximal end thereof, extruding the contrast medium from the distal end opening and the respective side apertures, and observing a motion of the distal end portion of the catheter. The amount Q1 of the contrast medium injected from the distal end opening and the total amount Q2 of the contrast medium injected from the respective side apertures have been measured to calculate the ratio of Q2/(Q1+Q2). The result of this experiment is given below in Table 1.

It is required to feed the contrast medium into the lumen in a total amount of 35 ml, under a pressure of 750 psi and at a flow rate of 10 ml/sec.

TABLE 1

|  | Q2/(Q1 + Q2) | Motion of the distal end portion of the catheter |
|---|---|---|
| Example 1 | 70% | No movement |
| Example 2 | 66% | No movement |
| Comparative Example 1 | — | About 10 cm to the right and about 15 cm upward |

As indicated by Table 1, the distal end portions of the catheters of Examples 1, 2 are not moved by injection of the contrast medium.

On the contrary, the distal end portion of the catheter of Comparative example 1 is moved by injection of the contrast medium.

Although the embodiments of the pigtail type catheter has been described hitherto, it is apparent that the angiographic catheter according to the present invention is not limited to the pigtail type.

As described hitherto, the angiographic catheter according to the present invention is able to inhibit the catheter from being moved or displaced by injection of the contrast medium. It is thus possible to perform the operation of image formation appropriately without disengaging or displacing the catheter from the desired part.

The aforementioned effect can be achieved strikingly especially in the case where the side apertures formed of the catheter at which the deformed portion is directed are arranged densely, where the diameter and the number of the side apertures to be formed are set as desired, and where the ratio of the amount of a liquid injected from the distal end opening to the total amount of the liquid injected from the respective apertures is set as desired.

By employing laser beam machining, especially by using an excimer laser, the side apertures can be formed easily with high processability as well as high precision, without causing process errors such as alteration, meltdown, flash or soot.

The angiographic catheter according to the present invention will be described hereinafter with reference to further embodiments as illustrated in the drawings.

Figure 6:
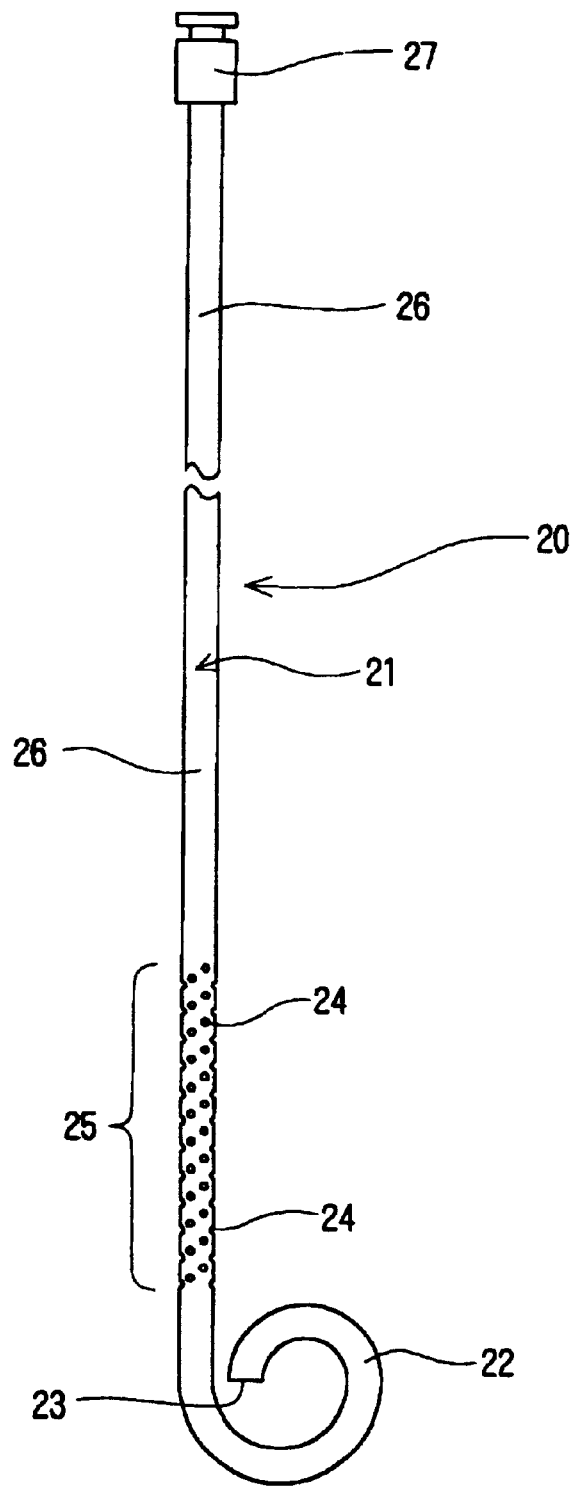
FIG. 6 is a partially omitted side view illustrating an embodiment of the angiographic catheter according to the present invention.
Figure 7:
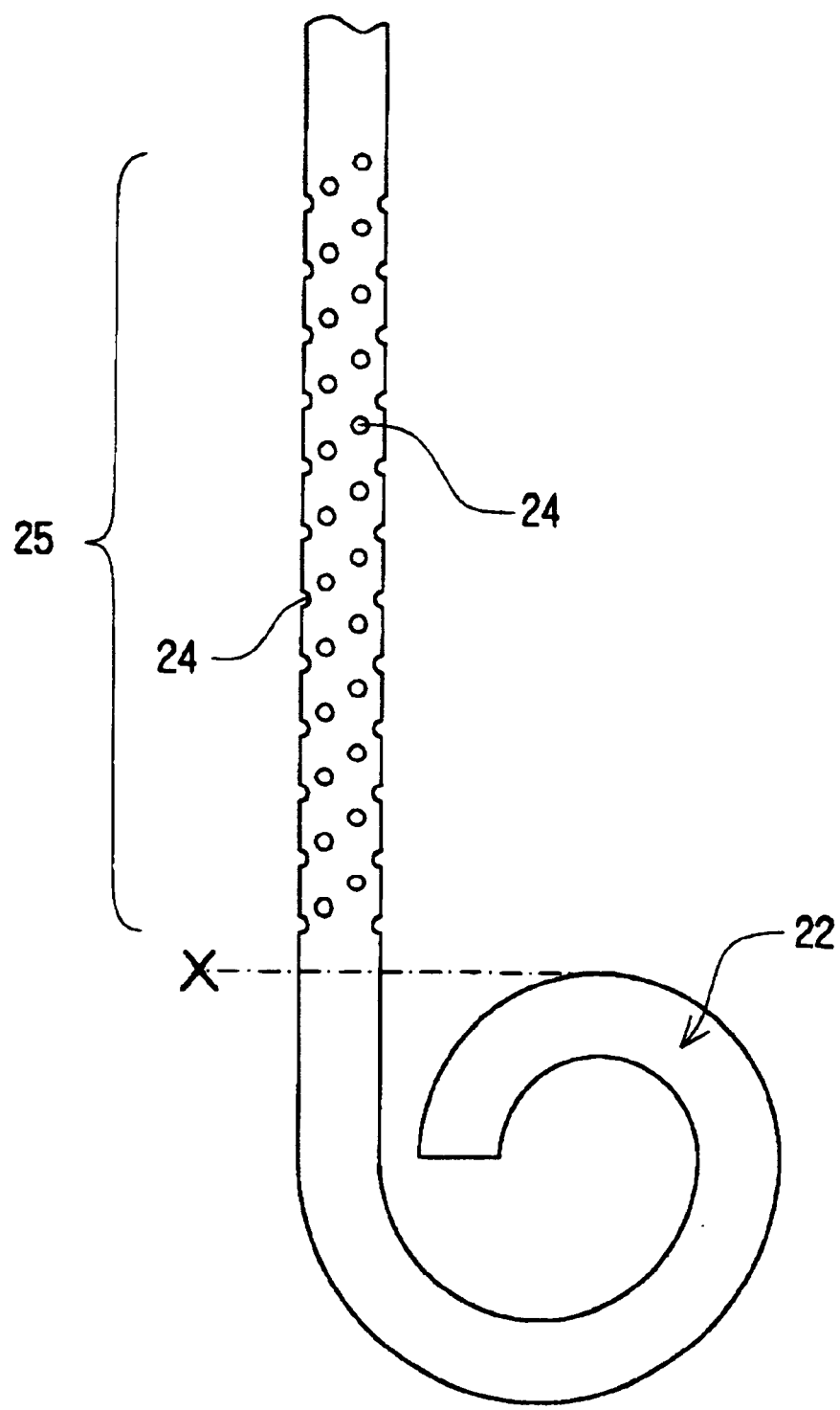
FIG. 7 is an enlarged view illustrating a distal end portion of the catheter as illustrated in FIG. 6.
Figure 8:
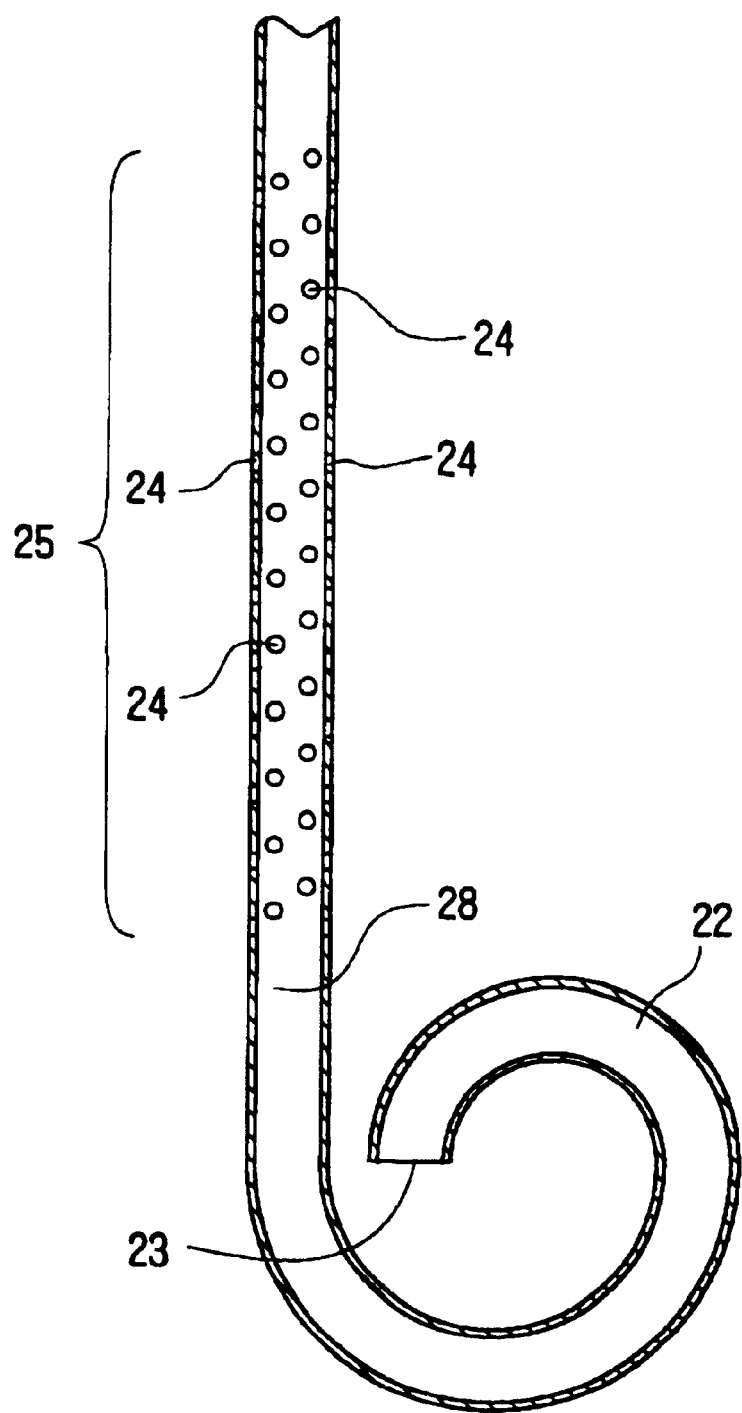
FIG. 8 is an enlarged sectional view illustrating the distal end portion of the catheter as illustrated in FIG. 6.

FIG. 6 is a partially omitted side view illustrating the angiographic catheter according to further embodiments of the present invention. FIG. 7 is an enlarged view illustrating the distal end portion of the catheter as illustrated in FIG. 6. FIG. 8 is an enlarged sectional view illustrating the distal end portion of the catheter as illustrated in FIG. 6.

An angiographic catheter 20 according to the present invention includes a catheter tube 21 having a lumen 28, a distal end opening 23 that communicates with the lumen 28, and side apertures 24 that communicate with the lumen 28. The side apertures 24 are provided to a predetermined section of a distal end portion of the catheter tube 21. The number of the side apertures 24 formed in an arbitrary portion of the predetermined section with an axial length of 10 mm is greater than 9, each of the side apertures 24 covering an area smaller than 0.3 mm$^2$. The side apertures 24 are preferably scattered over a predetermined section of a flank of a distal end portion of the catheter tube 21.

This catheter 20 is capable of aiding in the dispersal of a X-ray contrast medium. Hence, the contrast medium can be fed into a space corresponding to a desired part uniformly, and the amount of the contrast medium required to perform the operation of image formation sufficiently can be reduced. Furthermore, the impetus of the contrast medium flowing out of respective side apertures (a jet stream of the contrast medium) is weakened, so that a stimulus imparted to a lumina of a human is alleviated.

The angiographic catheter 20 according to the present invention is used to form an radiographic image of a lumina of a human such as blood vessels of a heart, a liver, a pancreas, a bile duct or the like.

The angiographic catheter 20 of this embodiment is designed to form an X-ray image of blood vessels of a heart. This catheter 20 has at a distal end portion thereof a deformed portion 22 that is curved like a pigtail. The catheter 20 exhibits elasticity as a whole and has at the distal end portion thereof the deformed portion 22 which is curved like a loop when no external force is applied thereto.

More specifically, the catheter 20 includes the catheter tube 21 and a hub 27 fixed to a proximal end of the catheter tube 21. The catheter tube 21 has the loop-like deformed portion 22, a side aperture forming portion 25 and a body portion 26 arranged in this order from the distal end thereof.

The catheter 20 may be made of a polyolefin such as polyethylene, polypropylene and a copolymer of ethylene and vinyl acetate, a polyolefin elastomer thereof, a polyamide resin (such as nylon 11, nylon 12 and nylon 6), a polyester polyamide resin (such as Grilax, a product of DIC Corp.), a polyeter polyamide resin (such as Pebax, a product of Atochem Corp.), polyurethane, ABS resin, a fluorine resin (such as PFA, PTFE and ETFE) or a soft fluorine resin, polyimide, a shape-memory resin, or various synthetic resins such as a polymer blend or a polymer alloy including the aforementioned materials (such as a polymer alloy of polyamide elastomer and polyurethane).

The catheter 20 is inserted into a lumina of a human, at which X-ray is beamed to identify a location thereof. Therefore, the catheter 20 may include a X-ray opaque substance such as barium sulfate, bismuth oxide and tungsten.

Furthermore, the loop-like deformed portion 22 is preferably more flexible than the side aperture portion 25 and the body portion 26. In this case, the material constituting the loop-like deformed portion 22 is more flexible than the material constituting the side aperture and body portions 25, 26. In other words, the former exhibits more elasticity than the latter. In order to ensure that the side aperture and body portions 25, 26 can be connected with each other easily and securely, it is desirable that a resin constituting the loop-like deformed portion 22 and a resin constituting the side aperture and body portions have compatibility with each other. In other words, these resins are thermodynamically dissoluble into each other, that is, they are inseparable from each other after they have been hardened.

It is desirable to select those resins whose properties are similar to each other. For example, the side aperture and body portions 25, 26 may be made of nylon 12 or a block copolymer of polythio and polyamide, while the loop-like deformed portion 22 may be made of another block copolymer of polyether and polyamide exhibiting more flexibility. In this case, the side apertures and body portions 25, 26 and the loop-like deformed portion 22 are both made of polyamide resin. Also, the side aperture and body portions 25, 26 may be made of a polyolefin elastomer (such as polyethylene elastomer), while the loop-like deformed portion 22 may be made of another polyolefin elastomer (such as polyethylene elastomer) exhibiting more flexibility. In this case, the side aperture and body portions 25, 26 and the loop-like deformed portion 22 are both made of polyolefin resin. Furthermore, the loop-like deformed portion 22 may be made of a polyester elastomer (containing a soft segment and a hard segment, the soft segment being in greater quantities), while the side aperture and body portions 25, 26 may be made of another polyester elastomer (containing a soft segment and a hard segment, the soft segment being outdone in quantity by the soft segment contained in the aforementioned loop-like deformed portion 22). In this case, the side aperture and body portions 25, 26 and the loop-like deformed portion 22 are both made of polyester resin. Furthermore, the side aperture and body portions 25, 26 may be made of a plasticized vinyl chloride resin, while the loop-like deformed portion 22 may be made of another plasticized vinyl chloride resin exhibiting more flexibility. In this case, the side aperture and body portions 25, 26 and the loop-like deformed portion 22 are both made of vinyl chloride resin. In addition, the loop-like deformed portion 22 may be made of polyurethane, while the side aperture and body portions 25, 26 may be made of a polymer alloy of polyamide elastomer and polyurethane. In this case, the side aperture and body portions 25, 26 and the loop-like deformed portion 22 are both made of polyurethane series.

Furthermore, the catheter 20 may have an outer layer entirely covering the loop-like deformed portion 22, the side aperture portion 25 and the body portion 26. The outer layer is preferably made of a material that can be adhered to the materials constituting the loop-like deformed portion 22 and the side aperture and body portions 25, 26, more specifically, a material consubstantial with or similar to those materials. For example, this outer layer may be made of a polyolefin such as polyethylene, polypropylene and a copolymer of ethylene and propylene, a thermoplastic resin such as polyvinyl chloride, a copolymer of ethylene and vinyl acetate and polyamide elastomer, a silicon rubber, a latex rubber or the like. The outer layer is preferably made of a polyamide elastomer or polyurethane which has been plasticized by a plasticizer such as para-oxy benzoic ethyl hexyl (POBO). In order to sleeken an outer surface of the catheter 20, it is preferable that the outer layer contain no X-ray opaque substance.

Furthermore, the outer layer (catheter tube) may be coated with a biomaterial, especially with an antithrombotic resin such as polyhydroxy ethyl meta-acrylate, a copolymer of hydroxy ethyl meta-acrylate and styrene (e.g., HEMA-St-HEMA block copolymer) or the like.

The catheter 20 has the lumen 28 formed therein. The lumen 28 extends from the rear end to the distal end of the catheter 20 and serves as a passage of a liquid such as a contrast medium. The lumen 28 opens at the distal end of the catheter 20, thus constituting the distal end opening 23. A guide wire (not shown) is inserted into the lumen 28, for example, when the catheter 20 is inserted into the lumina of a human. In the catheter 20 of this embodiment, the distal end opening 23 formed at the distal end of the loop-like deformed portion 22 is substantially parallel to the lumen 28 formed in the side aperture and body portions 25, 26 and is directed at the distal end of the catheter 20. Hence, if the shape of the loop-like deformed portion 22 remains unchanged, the contrast medium is discharged in a direction substantially parallel to the lumen 28 (axis) of the catheter 20.

Although not limited to any specific value, the catheter 20 has an outer diameter ranging preferably from 0.8 mm to 3.0 mm, more preferably, from 1.0 mm to 2.5 mm. Although not limited to any specific value, the catheter 20 has a thickness ranging preferably from 0.1 mm to 0.7 mm, more preferably, from 0.15 mm to 0.5 mm. The loop-like deformed portion 22 has a radius ranging preferably from 3.0 mm to 15.0 mm, more preferably from 3.0 to 8.0 mm.

The minute side apertures 24 are formed in the side aperture portion 25, which is located toward the proximal end of the catheter 20 from the loop-like deformed portion 22. The side apertures 24 are formed in a portion that is located toward the rear end of the catheter 20 from the rearmost portion of the loop-like deformed portion 22. In other words, the side apertures 24 are formed in a portion that is located toward the rear end of the catheter 20 from a location where a tangent X drawn from the rearmost portion of the loop-like deformed portion 22 crosses the catheter tube 21. The side aperture portion 25 has an axial length L ranging preferably from 5 mm to 80 mm, more preferably, from 10 mm to 45 mm. The side apertures 24 are preferably formed in a portion that is located 0 to 10 mm toward the rear end of the catheter 20 from the location where the tangent X drawn from the rearmost portion of the loop-like deformed portion 22 crosses the catheter tube 21. The side apertures 24 are more preferably formed in a portion that is located 1 to 8 mm toward the rear end of the catheter 20 from the tangent X.

The side apertures 24 are scattered substantially uniformly and entirely over the side aperture portion 25. The number of the side apertures 24 formed in an arbitrary section of the side aperture portion 25 with an axial length of 10 mm is greater than 9, each of the side apertures 24 covering an area smaller than 0.3 mm$^2$. The number of the side apertures 24 is counted based on a section of the side aperture portion 25 with a length of 10 mm where a maximum number of the side apertures 24 are formed. Any side aperture partially crossing the border of the aforementioned section is counted as one.

The side apertures 24 cover an area ranging preferably from 0.003 mm$^2$ to 0.3 mm$^2$, especially, from 0.008 mm$^2$ to 0.28 mm$^2$ and, more preferably, from 0.03 mm$^2$ to 0.25 mm$^2$.

The side apertures 24 have a (mean) diameter ranging preferably from 0.06 mm to 0.6 mm, more preferably, from 0.2 mm to 0.5 mm.

Figure 9:
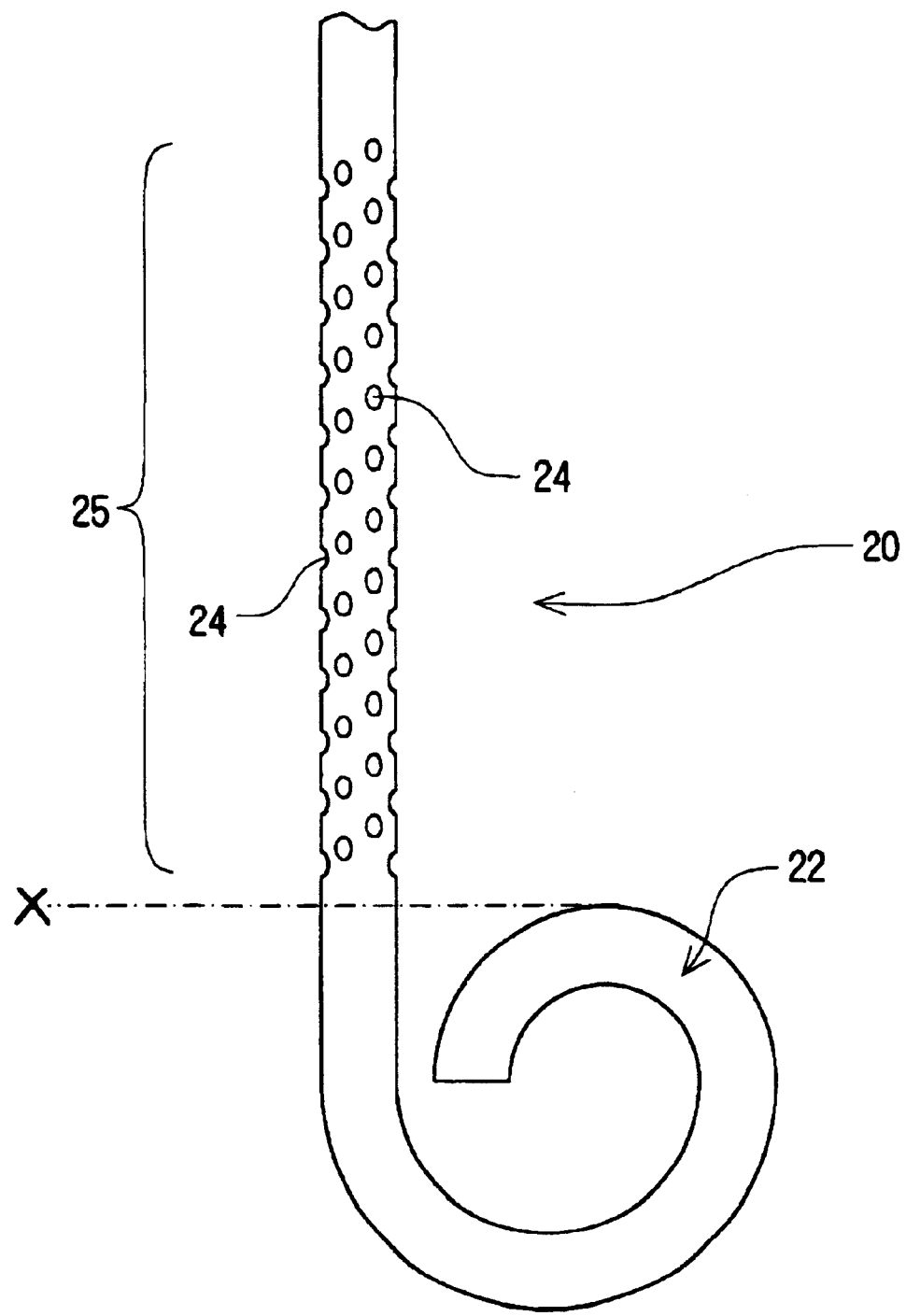
FIG. 9 is an enlarged view illustrating a distal end portion of an embodiment of the catheter.

The side aperture 24 is desirable an axially long ellipse or the oval of the catheter, as shown in FIG. 9. As the side apertures, the ratio with the length of the major axis to the minor axis length is desirably equal to or more than 1.2 mm and the minor axis length is desirable equal to or more than 0.06 mm. The ratio with the length of the major axis to the minor axis length is more desirable equal to or more than 1.3 and the minor axis length is desirable equal to or more than 0.2 mm. The oval to say here is the elliptical one which contains a straight line part.

The side aperture 24 is provided for the major axis in the side apertures to become parallel substantively with the axial direction of the catheter tube 21. The major axis in the side apertures may be rather diagonal to the axis of the catheter tube 21. The strength of the side apertures forming part 25 becomes high compared with the case to provide side apertures of the true circle with approximately the same area by making side apertures of the ellipse or the oval. The side apertures having a shape of the ellipse or the oval cover an area ranging preferably from 0.03 mm² to 0.3 mm².

The number of the side apertures 24 to be formed in an arbitrary section of the side aperture portion 25 with an axial length of 10 mm ranges preferably from 9 to 540, especially, from 9 to 500, more especially, from 9 to 240 and more preferably, from 10 to 120. If the number of the side apertures 24 is equal to or less than 500, the side aperture portion 25 is equipped with the enough tensile breaking strength. The total number of the side apertures 24 ranges preferably from 15 to 1,000, especially, from 15 to 240. The (mean) distance from one of the side apertures 24 to another ranges preferably from 0.3 mm to 10 mm, more preferably, from 0.5 mm to 8.0 mm.

The side apertures 24 cover a total area ranging preferably from 0.12 mm² to 300 mm², more preferably, from 0.45 mm² to 72 mm². The side apertures 24 formed in the section of the side aperture portion 25 with an axial length of 10 mm cover a total area ranging preferably from 0.072 mm² to 150 mm², more preferably, from 0.27 mm² to 70 mm², even more preferably, from 0.5 mm² to 30 mm², even more preferably, from 2.0 mm² to 15 mm².

The side apertures 24 are formed preferably such that the side aperture flow ratio of $Q2/(Q1+Q2)$ ranges from 0.25 to 0.9. It is to be noted that the amount of the contrast medium injected from the distal end opening 23 per one injection process is defined as Q1, and the total amount of the contrast medium injected from the respective side apertures 24 is defined as Q2. The side aperture flow ratio ranges preferably from 0.3 to 0.8, more preferably from 0.5 to 0.75, even more preferably, from 0.6 to 0.75. The aforementioned values have been obtained by injecting a the contrast medium (a viscosity of 10.6 c.p. at 37° C.) into the catheter 20 from the rear end thereof, in a total injection amount of 36 ml, under a pressure of 1000 psi and at a flow rate of 12 ml/sec.

Although the side apertures 24 can be formed by any possible process such as machining, it is especially preferable to use laser beam machining. This is because the side apertures 24 can be formed easily and the shape and dimension thereof can be controlled with precision. More preferably, a laser that oscillates at a wavelength within an ultraviolet region, for example, an excimer laser is used.

A hub 27 made of a hard or semi-hard synthetic resin (such as polycarbonate, polypropylene or polyamide) is attached to the proximal end of the catheter 21. A contrast medium injector (such as a syringe) can be attached to a rear end portion of the hub 27.

The examples of the angiographic catheter according to the present invention will be described hereinafter more concretely.

EXAMPLE 3

A catheter of Example 3 has been manufactured in the following manner. First, a tube with an outer diameter of 1.7 mm and an inner diameter of 1.2 mm is obtained by adding barium sulfate powder to a polymer alloy of polyamide elastomer and polyurethane, and a section with a length of 1,100 mm (a body tube) is cut off the tube obtained.

Then, a tube with an outer diameter of 1.7 mm and an inner diameter of 1.0 mm is obtained by adding barium sulfate powder to polyurethane, and a section with a length of about 33 mm (a curved tube) is cut off the tube obtained.

A connected tube is connecting to the curved tube to a distal end of the body tube by heating. Then, a hub made of nylon is attached to a rear end of the catheter tube.

The catheter tube has 6 rows of side apertures at intervals of 60° (each row consisting of 12 side apertures) formed in a section that is located 38 mm toward the proximal end from the distal end of the catheter tube and extends over an axial length of 24 mm or less. The distance between the centers of the adjacent side apertures (the distance between the side apertures that are arranged in the same row) is 2.0 mm. The side apertures assume the shape of an ellipse that covers an area of 0.27 mm² (with a dimension of 0.5 mm×0.7 mm). The total number of the side apertures is 72. In this catheter, the number of the side apertures formed in an arbitrary section of the side aperture portion with an axial length of 10 mm is 32. The side apertures formed in an arbitrary section of the side aperture portion with an axial length of 10 mm cover a total area of about 8.64 mm².

The side apertures are formed by laser beam machining using a KrF excimer laser that oscillates at a wavelength of 248 nm (with a power density of 0.5 kW/cm² on a surface of an object to be processed and with an irradiation time of 2.3 sec for each of the side apertures).

Then, the curved tube is heated to be made into a loop-like deformed portion which has a radius of curvature of about 6 mm. Consequently, a catheter for angiography or radiography as illustrated in FIG. 6 is obtained.

The side apertures are formed in a portion that is located 3 mm toward the rear end of the catheter from a location where a tangent X drawn from the rearmost portion of the loop-like deformed portion crosses the catheter tube. The distal end opening of the catheter is substantially parallel to the lumen formed in the side aperture and body portions of the catheter and is directed at the distal end of the catheter. The side aperture portion has a tensile breaking strength greater than 1.6 kg.

EXAMPLE 4

Another catheter of Example 4 has been manufactured, which is similar to that of Example 3 except that the conditions concerning the distal end opening and the side apertures are changed as follows.

The catheter tube has 6 rows of side apertures at intervals of 60° (each row consisting of 3 side apertures) formed in a section that is located 38 mm toward the proximal end from the distal end of the catheter tube and extends over an axial length of 20.7 mm or less. The distance between the centers of the adjacent side apertures (the distance between the side apertures that are arranged in the same row) is 7.5 mm. The side apertures assume the shape of an ellipse that covers an area of 0.27 mm² (with a dimension of 0.5 mm×0.7 mm). The total number of the side apertures is 18. In this catheter, the number of the side apertures formed in an arbitrary section of the side aperture portion with an axial length of 10 mm is 10. The side apertures formed in an arbitrary section of the side aperture portion with an axial length of 10 mm cover a total area of about 2.7 mm². The side aperture portion has a tensile breaking strength greater than 1.6 kg.

EXAMPLE 5

Still another catheter of Example 5 has been manufactured, which is similar to that of Example 3 except that the conditions concerning the distal end opening and the side apertures are changed as follows.

The catheter tube has 24 rows of side apertures at intervals of 15° (each row consisting of 40 side apertures) formed in a section that is located 38 mm toward the proximal end from the distal end of the catheter tube and extends over an axial length of 20 mm or less. The distance between the centers of the adjacent side apertures (the distance between the side apertures that are arranged in the same row) is 0.5 mm. The side apertures assume the shape of a circle that covers an area of 0.03 mm$^2$ (with a dimension of 0.2 mm). The total number of the side apertures is 960. In this catheter, the number of the side apertures formed in an arbitrary section of the side aperture portion with an axial length of 10 mm is 480. The side apertures formed in an arbitrary section of the side aperture portion with an axial length of 10 mm cover a total area of about 14.4 mm$^2$. The side aperture portion has a tensile breaking strength greater than 1.6 kg.

EXAMPLE 6

Still another catheter of Example 6 has been manufactured, which is similar to that of Example 3 except that the conditions concerning the distal end opening and the side apertures are changed as follows.

The catheter tube has 24 rows of side apertures at intervals of 15° (each row consisting of 45 side apertures) formed in a section that is located 38 mm toward the proximal end from the distal end of the catheter tube and extends over an axial length of 20 mm or less. The distance between the centers of the adjacent side apertures (the distance between the side apertures that are arranged in the same row) is 0.45 mm. The side apertures assume the shape of a circle that covers an area of 0.03 mm$^2$ (with a dimension of 0.2 mm). The total numer of the side apertures is 1080. In this catheter, the number of the side apertures formed in an arbitrary section of the side aperture portion with an axial length of 10 mm is 540. The side apertures formed in an arbitrary section of the side aperture portion with an axial length of 10 mm cover a total area of about 16.2 mm$^2$. The side aperture portion has a tensile breaking strength of 1.5 kg.

EXAMPLE 7

Still another catheter of Example 7 has been manufactured, which is similar to that of Example 3 except that the conditions concerning the distal end opening and the side apertures are changed as follows.

The catheter tube has 24 rows of side apertures at intervals of 15° (each row consisting of 40 side apertures) formed in a section that is located 38 mm toward the proximal end from the distal end of the catheter tube and extends over an axial length of 19.6 mm or less. The distance between the centers of the adjacent side apertures (the distance between the side apertures that are arranged in the same row) is 0.5 mm. The side apertures assume the shape of a circle that covers an area of 0.011 mm$^2$ (with a dimension of 0.12 mm). The total number of the side apertures is 960. In this catheter, the number of the side apertures formed in an arbitrary section of the side aperture portion with an axial length of 10 mm is 480. The side apertures formed in an arbitrary section of the side aperture portion with an axial length of 10 mm cover a total area of about 5.28 mm$^2$. The side aperture portion has a tensile breaking strength greater than 1.6 kg.

EXAMPLE 8

Still another catheter of Example 8 has been manufactured, which is similar to that of Example 3 except that the conditions concerning the distal end opening and the side apertures are changed as follows.

The catheter tube has 24 rows of side apertures at intervals of 15° (each row consisting of 40 side apertures) formed in a section that is located 38 mm toward the proximal end from the distal end of the catheter tube and extends over an axial length of 19.6 mm or less. The distance between the centers of the adjacent side apertures (the distance between the side apertures that are arranged in the same row) is 0.5 mm. The side apertures assume the shape of a circle that covers an area of 0.005 mm$^2$ (with a dimension of 0.08 mm). The total number of the side apertures is 960. In this catheter, the number of the side apertures formed in an arbitrary section of the side aperture portion with an axial length of 10 mm is 480. The side apertures formed in an arbitrary section of the side aperture portion with an axial length of 10 mm cover a total area of about 2.4 mm$^2$. The side aperture portion has a tensile breaking strength greater than 1.6 kg.

EXAMPLE 9

Still another catheter of Example 9 has been manufactured, which is similar to that of Example 3 except that the conditions concerning the distal end opening and the side apertures are changed as follows.

The catheter tube has 6 rows of side apertures at intervals of 60° (each row consisting of 40 side apertures) formed in a section that is located 38 mm toward the proximal end from the distal end of the catheter tube and extends over an axial length of 19.8 mm or less. The distance between the centers of the adjacent side apertures (the distance between the side apertures that are arranged in the same row) is 0.5 mm. The side apertures assume the shape of a circle that covers an area of 0.05 mm$^2$ (with a dimension of 0.25 mm). The total number of the side apertures is 240. In this catheter, the number of the side apertures formed in an arbitrary section of the side aperture portion with an axial length of 10 mm is 120. The side apertures formed in an arbitrary section of the side aperture portion with an axial length of 10 mm cover a total area of about 6 mm$^2$. The side aperture portion has a tensile breaking strength greater than 1.6 kg.

EXAMPLE 10

Still another catheter of Example 10 has been manufactured, which is similar to that of Example 3 except that the conditions concerning the distal end opening and the side apertures are changed as follows.

The catheter tube has 12 rows of side apertures at intervals of 30° (each row consisting of 40 side apertures) formed in a section that is located 38 mm toward the proximal end from the distal end of the catheter tube and extends over an axial length of 19.7 mm or less. The distance between the centers of the adjacent side apertures (the distance between the side apertures that are arranged in the same row) is 0.5 mm. The side apertures assume the shape of a circle that covers an area of 0.03 mm$^2$ (with a dimension of 0.2 mm). The total number of the side apertures is 480. In this catheter, the number of the side apertures formed in an arbitrary section of the side aperture portion with an axial length of 10 mm is 240. The side apertures formed in an arbitrary section of the side aperture portion with an axial length of 10 mm cover a total area of about 7.2 mm$^2$. The side aperture portion has a tensile breaking strength greater than 1.6 kg.

EXAMPLE 11

Still another catheter of Example 11 has been manufactured, which is similar to that of Example 3 except that the conditions concerning the distal end opening and the side apertures are changed as follows.

The catheter tube has 5 rows of side apertures at intervals of 72° (each row consisting of 20 side apertures) formed in a section that is located 38 mm toward the proximal end from the distal end of the catheter tube and extends over an axial length of 19.5 mm or less. The distance between the centers of the adjacent side apertures (the distance between the side apertures that are arranged in the same row) is 1 mm. The side apertures assume the shape of a circle that covers an area of 0.2 mm² (with a dimension of 0.5 mm). The total number of the side apertures is 100. In this catheter, the number of the side apertures formed in an arbitrary section of the side aperture portion with an axial length of 10 mm is 50. The side apertures formed in an arbitrary section of the side aperture portion with an axial length of 10 mm cover a total area of about 10 mm². The side aperture portion has a tensile breaking strength greater than 1.6 kg.

COMPARATIVE EXAMPLE 2

Still another catheter of Comparative example 2 has been manufactured, which is similar to that of Example 3 except that the conditions concerning the distal end opening and the side apertures are changed as follows.

The catheter tube has 6 side apertures formed in a section that is located 38 mm toward the proximal end from the distal end of the catheter tube and extends over an axial length of 13.3 mm or less. The distance between the centers of the adjacent side apertures (the distance between the side apertures that are arranged in the same row) is 2.5 mm. The side apertures assume the shape of a circle that covers an area of 0.5 mm² (with a dimension of 0.8 mm). In this catheter, the number of the side apertures formed in an arbitrary section of the side aperture portion with an axial length of 10 mm is 5. The side apertures formed in an arbitrary section of the side aperture portion with an axial length of 10 mm cover a total area of about 2.5 mm². The side aperture has a tensile breaking strength greater than 1.6 kg.

EXPERIMENT 2

An experiment has been conducted on the catheters of Examples 3 through 8 and Comparative example 2 to test the dispersability of the contrast medium, the mean flow rate of the contrast medium per unit area of each of the side apertures, and the side apertures flow ratio. The result is given in Table 2.

This experiment includes the step of injecting the contrast medium (a viscosity of 10.6 c.p. at 37° C.) into the catheter from the rear end thereof, in a total injection amount of 36 ml, under a pressure of 1000 psi and at a flow rate of 12 ml/sec. The dispersability of the simulant of the contrast medium is tested in a water tank by adding red ink thereto, so that the dispersability thereof is visibly scrutable. Referring to Table 2, the symbols ⊚, ○ and X indicate that the X-ray contrast medium is very well dispersed, well dispersed, and insufficiently dispersed respectively.

By measuring the amount Q1 of the contrast medium injected from the distal end opening and the total amount Q2 of the contrast medium injected from the respective side apertures, the side aperture flow ratio Q2/(Q1+Q2) is obtained.

TABLE 2

| | Dispersability | Mean flow rate per unit area of each of the side apertures (ml/s)/mm² | Q2/(Q1 + Q2) |
| --- | --- | --- | --- |
| Example 3 | ⊚ | 0.44 | 0.72 |
| Example 4 | ○ | 1.51 | 0.64 |
| Example 5 | ○ | 0.29 | 0.62 |
| Example 6 | ○ | 0.25 | 0.70 |
| Example 7 | ○ | 0.19 | 0.32 |
| Example 8 | ○ | 0.13 | 0.27 |
| Example 9 | ○ | 0.42 | 0.61 |
| Example 10 | ○ | 0.32 | 0.55 |
| Example 11 | ○ | 0.39 | 0.68 |
| Comparative Example 2 | X | 2.65 | 0.67 |

While the present invention has been described with reference to preferred embodiments thereof, it is to be understood that the invention is not limited to the disclosed embodiments or constructions. On the contrary, the invention is intended to cover various modifications and equivalent arrangements included within the spirit and scope of the appended claims.

What is claimed is:

1. An angiographic catheter exhibiting elasticity and having at a distal end portion a deformed portion that is curved in a loop when no external force is applied thereto, said deformed portion having at a distal end thereof a distal end opening, wherein a plurality of side apertures are formed in a straight portion of the catheter that is located toward a proximal end of said catheter from said deformed portion, said deformed portion, including said distal end opening, being designed such that a jet stream of a contrast medium injected from the distal end opening flows substantially perpendicularly to the axis of the straight portion in which the side apertures are formed when the contrast medium is injected from the distal end opening, said side apertures being arranged densely in a flank of the catheter at which said deformed portion is directed and such that a reaction force generated by injection of the contrast medium fed through a lumen of said catheter from said distal end opening is counterbalanced to the greatest possible extent by the contrast medium injected from said side apertures, and wherein upon a quantity of contrast medium being fed into the lumen a ratio of Q2/(Q1+Q2) ranges from 0.5 to 0.9, with Q1 representing the amount of the contrast medium injected from said distal end opening and Q2 representing the total amount of the contrast medium injected from said side apertures.

2. The angiographic catheter according to claim 1, wherein said side apertures have a diameter ranging from 0.2 mm to 0.7 mm.

3. The angiographic catheter according to claim 1, wherein the catheter includes 25 to 100 side apertures.

4. The angiographic catheter according to claim 1, wherein said side apertures possess an elliptical or oval shape that is elongated along an axis of the catheter.

5. The angiographic catheter according to claim 1, wherein said side apertures and said deformed portion including said distal end opening are designed such that a vectorial sum of a jet force generated by the contrast medium injected from the distal end opening and a jet force generated by the contrast medium injected from the side apertures is approximately null.

6. The angiographic catheter according to claim 1, wherein said side apertures are formed in the flank of the catheter at which the deformed portion is directed and a central angle of an area over which the side apertures are formed is from 100° to 200°.

7. The angiographic catheter according to claim 1, including a number of side apertures formed in a flank portion of the catheter that is opposite to a portion at which the deformed portion is directed.

8. The angiographic catheter according to claim 1, wherein the ratio of Q2/(Q1+Q2) ranges from 0.5 to 0.9 when the contrast medium with a viscosity of 10.6 cps is fed into the catheter from the proximal end thereof in a total amount of 35 ml, under a pressure of 750 psi and at a flow rate of 10 ml/sec.

9. An angiographic catheter comprising a catheter tube having a lumen, a loop-shaped deformed portion having a distal end opening communicating with said lumen, a side aperture forming portion having a number of side apertures communicating with said lumen, and a body portion, said side apertures being formed in a flank of the catheter that is located toward a proximal end of said catheter from said deformed portion, the body portion being located toward a proximal end of said catheter from said side aperture forming portion, there being more than 9 side apertures formed in a section of said side aperture forming portion having an axial length of 10 mm, with each of said side apertures covering an area smaller than 0.3 mm$^2$, and said side apertures formed in the section of said side aperture forming portion having an axial length of 10 mm covering a total area ranging from 2.0 mm$^2$ to 15 mm$^2$, said side apertures being formed such that a ratio of Q2/(Q1+Q2) ranges from 0.25 to 0.9 when an amount of the contrast medium injected from said distal end opening is defined as Q1 and a total amount of the contrast medium injected from said side apertures is defined as Q2.

10. The angiographic catheter according to claim 9, wherein said side apertures are scattered entirely over the side aperture forming portion.

11. The angiographic catheter according to claim 9, wherein the number of said side apertures formed in a section of said side apertures forming portion having an axial length of 10 mm is smaller than 500.

12. The angiographic catheter according to claim 11, wherein each of said side apertures covers an area greater than 0.008 mm$^2$.

13. The angiographic catheter according to claim 9, wherein said distal end opening of said catheter is substantially parallel to an axis of the body portion of said catheter.

14. The angiographic catheter according to claim 11, wherein said side apertures is an axially long ellipse or oval of the catheter.

15. The angiographic catheter according to claim 9, wherein the side apertures are formed in a portion that is located toward the proximal end of the catheter from a location and which a tangent drawn from a rearmost portion of the deformed portion curved in a loop-shaped manner crosses the catheter tube.

16. The angiographic catheter according to claim 9, wherein said loop-shaped deformed portion is more flexible than the side aperture portion and the body portion.

17. The angiographic catheter according to claim 9, wherein said distal end opening of said catheter is substantially parallel to an axis of the side aperture forming portion of said catheter.

18. The angiographic catheter according to claim 9, wherein the catheter has a mean flow rate of the contrast medium per unit area of each of the side aperture ranging from 0.13 (ml/s)/mm$^2$ to 1.51 (ml/s)/mm$^2$ when the contrast medium with a viscosity of 10.6 c.p. at 37° C. is injected into the catheter from a rear end thereof in a total injection amount of 36 ml under a pressure of 1000 psi and at a flow rate of 12 ml/sec.

19. The angiographic catheter according to claim 9, wherein the ratio of Q2/(Q1+Q2) ranges from 0.25 to 0.9 when the contrast medium with a viscosity of 10.6 c.p. at 37° C. is injected into the catheter from a rear end thereof, in a total injection amount of 36 ml, under a pressure of 1000 psi and at a flow rate of 12 ml/sec.

20. The angiographic catheter according to claim 9, wherein said side apertures are formed such that a ratio of Q2/(Q1+Q2) ranges from 0.3 to 0.8 when the amount of the contrast medium injected from said distal end opening is defined as Q1 and the total amount of the contrast medium injected from said side apertures is defined as Q2.

21. The angiographic catheter according to claim 20, wherein the ratio of Q2/(Q1+Q2) ranges from 0.3 to 0.8 when the contrast medium with a viscosity of 10.6 c.p. at 37° C. is injected into the catheter from a rear end thereof, in a total injection amount of 36 ml, under a pressure of 1000 psi and at a flow rate of 12 ml/sec.

22. An angiographic catheter comprising a catheter tube having a lumen, a loop-shaped deformed portion having a distal end opening communicating with said lumen, a side aperture forming portion having a number of side apertures communicating with said lumen, and a body portion, said side apertures being formed in a flank of the catheter that is located toward a proximal end of said catheter from said deformed portion, the body portion being located toward a proximal end of said catheter from said side aperture forming portion, there being more than 9 side apertures formed in a section of said side aperture forming portion having an axial length of 10 mm, with each of said side apertures covering an area smaller than 0.3 mm$^2$, the catheter having a mean flow rate of the contrast medium per unit area of each of the side apertures ranging from 0.13 (ml/s)/mm$^2$ to 1.51 (ml/s)/mm$^2$ when the contrast medium with a viscosity of 10.6 c.p. at 37° C. is injected into the catheter from a rear end thereof in a total injection amount of 36 ml under a pressure of 1000 psi and at a flow rate of 12 ml/sec, said side apertures being formed such that a ratio of Q2/(Q1+Q2) ranges from 0.25 to 0.9 when an amount of the contrast medium injected from said distal end opening is defined as Q1 and a total amount of the contrast medium injected from said side apertures is defined as Q2.

23. The angiographic catheter according to claim 22, wherein said side apertures are scattered entirely over the side aperture forming portion.

24. The angiographic catheter according to claim 22, wherein there are less than 500 side apertures formed in a section of said side aperture forming portion having an axial length of 10 mm.

25. The angiographic catheter according to claim 22, wherein each of said side apertures covers an area greater than 0.008 mm$^2$.

26. The angiographic catheter according to claim 22, wherein a distal end of said catheter is a deformed portion curved in a loop, and wherein said side apertures are formed in a flank of the catheter located toward a proximal end of said catheter from said deformed portion.

27. The angiographic catheter according to claim 22, wherein said distal end opening of said catheter is substantially parallel to an axis of the body portion of said catheter.

28. The angiographic catheter according to claim 22, wherein said side apertures possess an elliptical or oval shape that is elongated along an axis of the catheter.

29. An angiograhic catheter exhibiting elasticity and having a lumen and a distal end portion possessing a deformed portion that is curved in a loop in the absence of an applied external force, the deformed portion having a distal end at which is located a distal end opening, the catheter including a straight portion located toward a proximal end of the catheter from the deformed portion, the straight portion possessing an axis and being provided with a plurality of side apertures, the deformed portion being oriented so that a jet stream of a contrast medium injected from the distal end opening flows substantially perpendicularly to the axis of the straight portion in which the side apertures are formed when the contrast medium is injected from the distal end opening, the side apertures being arranged such that a reaction force generated by injection of the contrast medium fed through the lumen of the catheter from the distal end opening is counterbalanced to the greatest possible extent by the contrast medium injected from the side apertures, and wherein upon a quantity of contrast medium being fed into the lumen a ratio of $Q2/(Q1+Q2)$ ranges from 0.5 to 0.9, with Q1 representing the amount of the contrast medium injected from said distal end opening and Q2 representing the total amount of the contrast medium injected from said side apertures.

30. The angiographic catheter according to claim 29, wherein the ratio of $Q2/(Q1+Q2)$ ranges from 0.5 to 0.9 when the contrast medium with a viscosity of 10.6 cps is fed into the catheter from the proximal end thereof in a total amount of 35 ml, under a pressure of 750 psi and at a flow rate of 10 ml/sec.

* * * * *

UNITED STATES PATENT AND TRADEMARK OFFICE
CERTIFICATE OF CORRECTION

PATENT NO. : 6,280,434 B1
DATED : August 28, 2001
INVENTOR(S) : Yasushi Kinoshita et al.

It is certified that error appears in the above-identified patent and that said Letters Patent is hereby corrected as shown below:

Title page,
Item [56] References Cited
U.S. PATENT DOCUMENTS
"4,913,683    *    4/1990    Gregory..........................604/8"
is changed to read
-- 4,931,683    *    4/1990    Gregory..........................604/8 --

Column 17,
Line 48, delete " 11 " and insert -- 9 --.
Line 66, delete "aperture" and insert -- apertures --.

Signed and Sealed this

Twenty-eighth Day of May, 2002

Attest:

Attesting Officer

JAMES E. ROGAN
Director of the United States Patent and Trademark Office